(12) United States Patent
Djonov et al.

(10) Patent No.: US 9,649,298 B2
(45) Date of Patent: May 16, 2017

(54) CYTOTOXIC SUBSTANCE FOR USE IN COMBINATION WITH RADIOTHERAPY IN CANCER TREATMENT

(71) Applicants: Fumedica AG, Muri (CH); Universität Bern, Bern (CH)

(72) Inventors: Valentin Djonov, Kehrsatz (CH); Beat Steger, Sobrio (CH)

(73) Assignees: Fumedica AG, Muri (CH); Universität Bern, Bern (CH)

( * ) Notice: Subject to any disclaimer, the term of this patent is extended or adjusted under 35 U.S.C. 154(b) by 0 days.

(21) Appl. No.: 14/896,055

(22) PCT Filed: Jun. 4, 2014

(86) PCT No.: PCT/EP2014/061628
§ 371 (c)(1),
(2) Date: Dec. 4, 2015

(87) PCT Pub. No.: WO2014/195374
PCT Pub. Date: Dec. 11, 2014

(65) Prior Publication Data
US 2016/0128983 A1   May 12, 2016

(30) Foreign Application Priority Data

Jun. 4, 2013 (EP) .................................... 13170442

(51) Int. Cl.
| | |
|---|---|
| *A61K 31/4188* | (2006.01) |
| *A61K 41/00* | (2006.01) |
| *A61K 45/06* | (2006.01) |
| *A61K 31/495* | (2006.01) |
| *A61K 31/555* | (2006.01) |
| *A61K 31/655* | (2006.01) |
| *A61K 33/24* | (2006.01) |
| *A61K 38/18* | (2006.01) |
| *A61N 5/10* | (2006.01) |

(52) U.S. Cl.
CPC ........ *A61K 31/4188* (2013.01); *A61K 31/495* (2013.01); *A61K 31/555* (2013.01); *A61K 31/655* (2013.01); *A61K 33/24* (2013.01); *A61K 38/1866* (2013.01); *A61K 41/0038* (2013.01); *A61K 45/06* (2013.01); *A61N 5/10* (2013.01); *A61N 2005/1098* (2013.01)

(58) Field of Classification Search
CPC .................................................. A61K 31/4188

USPC ......................................................... 514/398
See application file for complete search history.

(56) References Cited

U.S. PATENT DOCUMENTS

2010/0329413 A1   12/2010   Zhou et al.

FOREIGN PATENT DOCUMENTS

EP   2 374 463 A1   10/2011

OTHER PUBLICATIONS

P. Lelieveld, et al., "The Effect of Treatment in Fractionated Schedules With the Combination of X-Irradiation and Six Cytotoxic Drugs on the RIF-1 Tumor and Normal Mouse Skin", International Journal of Radiation: Oncology Biology Physics, Jan. 1, 1985, pp. 111-121, vol. 11, No. 1.
Peter R. Twentyman, et al., "The Effect of Time Between X-Irradiation and Chemotherapy on the Growth of Three Solid Mouse Tumors. III. CIS-Diamminedichloroplatinum", International Journal of Radiation: Oncology Biology Physics, Aug. 1, 1979, pp. 1365-1367, vol. 5, No. 8.
Adrian C. Begg, et al., "Combination Therapy of a Solid Murine Tumor With 1, 3 Bis (2-Chloroethyl)-1-Nitrosourea and Irradiation", International Journal of Radiation: Oncology Biology Physics, Sep. 1, 1979, pp. 1559-1563, vol. 5, No. 9.
Marie-Claude Biston, et al., "Cure of Fisher Rats Bearing Radioresistant F98 Glioma Treated with cis-Platinum and Irradiated with Monochromatic Synchrotron X-Rays", Cancer Research, Apr. 1, 2004, pp. 2317-2323, vol. 64, No. 7.
International Search Report for PCT/EP2014/061628 dated Jul. 14, 2014 [PCT/ISA/210].
Thomas et al., "Effects of flattening filter-free and volumetric-modulated arc therapy delivery on treatment efficiency", Journal of Applied Clinical Medical Physics, 2013, vol. 14, No. 6, pp. 155-166.
Clark MD et al., "Plan quality and treatment planning technique for single isocenter cranial radiosurgery with volumetric modulated arc therapy", Practical Radiation Oncology, 2012, vol. 2, pp. 306-313.

*Primary Examiner* — Taofiq A Solola
(74) *Attorney, Agent, or Firm* — Sughrue Mion, PLLC

(57) ABSTRACT

The present invention provides a substance comprising a preparation of at least one chemotherapeutic or cytotoxic substance for the use in treatment of a disease of a mammalian patient, especially in the treatment of cancer. The invention suggests a symbiotic or synergistic combination of radiotherapy and chemotherapeutic or cytotoxic drug delivery.

14 Claims, 7 Drawing Sheets

CYTOTOXIC SUBSTANCE FOR USE IN COMBINATION WITH RADIOTHERAPY IN CANCER TREATMENT

CROSS REFERENCE TO RELATED APPLICATIONS

This application is a National Stage Entry of International Application No. PCT/EP2014/061628 filed Jun. 4, 2014, claiming priority based on European Patent Application No. 13170442.1 filed Jun. 4, 2013, the contents of all of which are incorporated herein by reference in their entirety.

TECHNICAL FIELD

The present invention relates to a preparation comprising cytotoxic substances for use in the treatment of cancer by radiotherapy, preferably in the treatment of irradiated tumor tissue, especially in the treatment of irradiated malignant tumor tissue of the mammalian brain or lung. The invention further relates to a method of administration of such a preparation and a method of treatment of cancer using such a preparation.

PRIOR ART

Despite the risks of direct interventions, surgery is still the method of choice for curative cancer treatment. However, surgery is not applicable in the case of large inoperable or multiple small tumors, especially certain kinds of brain and lung tumors. Therefore, radiotherapy or chemotherapy are sequential standard treatments for such situations in order to slow recurrent disease and suppress tumor growth.

Especially for glioblastoma, chemotherapy followed by subsequent radiotherapy was found to double the median survival rate. The beneficial effect of radiotherapy is believed to originate from the fact that cells of the tumor tissue absorb a lethal dose of energy upon interaction with the beam, i.e. when being present in the direction of propagation, i.e. the beam axis, of the electro-magnetic or corpuscular radiation. Consequently, radiotherapy is far from being selective on the type of tissue (malignant or not). Thus, dosing and focusing of the beam energy are highly crucial to avoid excessive damage of healthy tissue. Therefore, precisely targeted three-dimensional conformal radiotherapy is favourable (as shown by Clark G M et al., Plan quality and treatment planning for single isocenter cranial radiosurgery with volumetric modulated arc therapy, Practical Radiation Oncology, 2012 October; 2(4):306-313; and by Thomas E M et al., Effects of flattening filter-free and volumetric-modulated arc therapy delivery on treatment efficiency, Journal of Applied Clinical Medical Physics, 2013 May 6; 14(3):4126). In such applications, a total radiation dose of less than 100 Grays (Gy) were found to be optimal.

Recent advances in research surprisingly suggest that highly energetic deceleration radiation (so-called Bremsstrahlung) of charged particles (e.g. electrons, ions) in the form of synchrotron radiation may be used in radiotherapy. A synchrotron is a particular type of cyclic particle accelerator originating from the cyclotron in which the guiding magnetic field (bending the particles into a closed path) is time-dependent, being synchronized to a particle beam of increasing kinetic energy. In a synchrotron, the adaptation of the increasing relativistic mass of particles during acceleration is done by variation of the magnetic field strength in time, rather than in space. For particles that are not close to the speed of light, the frequency of the applied electromagnetic field may also change to follow their non-constant circulation time. By increasing these parameters accordingly as the particles gain energy, their circulation path can be held constant as they are accelerated. Synchrotron radiation covers a broad continuous spectrum (microwaves to hard X-rays; 1 to $10^5$ kilo electronvolt (keV)) at a high intensity and brilliance. The high intensity allows for absorption doses of around 100 Gy to several thousand Grays. Such beam impact is usually not suitable for in vivo treatments. It has been shown that a therapeutic effect on tumors, especially glioblastoma, or carcinomas of the lung, especially those which derive from epithelial cells, may be achieved when making use of the spectral range from 50 to 600 keV and collimating the short pulsed (less than 1 s) radiation into fans or arrays of highly parallel beams of microscopic cross-section, with a low divergence, and an inter-beam distance of some hundred micrometers. However, it has been found that such focused microbeam irradiation results in microscopic regions of damaged cells which are rapidly cured, which is why this type of irradiation does not have a lethal effect on the tumor nor on the surrounding benign tissue of the organ. While the lethal effect is what is usually desired in conventional cancer therapy, a non-lethal impact on the healthy tissue would be favourable. US 2010/00329413 A1 suggests the use of non-synchrotronic source as an alternative for microbeam radiation therapy, however, here too, it is admitted that very high radiation doses are necessary to be effective in cancer therapy.

In the hope of increasing selectivity of the cancer treatment, of treating tumor cells which form small tissue structures that cannot easily be targeted, and of further decreasing the necessary exposure to radiation, chemotherapy was already proposed to be combined with the surgery and/or radiotherapy. But, so far, only the administration of the drug substance temozolomide prior to radiotherapy showed promising results. While temozolomide is moderately cytotoxic, it seems to sensitize the tumor cells to radiation. Its delivery however remains the only standard treatment of glioblastoma, when radiotherapy and chemotherapy are combined. Delivery of other cytotoxic drug substances were investigated, however failed to provide a symbiotic or synergistic effect of radiotherapy and chemotherapy.

SUMMARY OF THE INVENTION

It is the aim of the present invention to overcome the above mentioned disadvantages of the state-of-the-art preparations and their delivery methods in disease treatment, especially in tumor treatment.

According to a first embodiment of the invention, a preparation comprising at least one chemotherapeutic or cytotoxic substance is provided for the use in treatment of a disease of a mammalian patient. The preparation and its delivery method have been shown to be especially advantageous in the treatment of cancer, especially brain tumors, such as glioblastoma. The treatment according to the current invention comprises at least the following steps:

transmittal of a therapeutically active, substantially non-cytotoxic dose of radiation to a tissue, preferably a tumor tissue of a patient, wherein the dose of radiation is adapted to generate at least one microscopic damage region in at least one boundary wall structure of a supply portion of the tissue, preferably a blood vessel; and subsequently administration of the preparation to the patient such that the chemotherapeutic or cytotoxic substance and/or a metabolic derivative thereof reaches the at least one microscopic damage region before the at least one microscopic damage region is substantially or completely cured by endogenous tissue repair. In other words, the present invention concerns a preparation comprising at least one chemotherapeutic or cytotoxic substance for use in treatment of a tumor tissue irradiated in a boundary wall structure of a supply portion of the tumor tissue by a therapeutically active dose of radiation.

The at least one microscopic damage region in at least one boundary wall structure contains one or more microscopic lesions or defects in the tissue affected by the radiation. The damage area essentially corresponds to the cross-section of the beam or the sum of beams directed towards the tissue to be aimed at by the radiation. The type of cell damage can vary, depending on type, dose and duration of radiation, as well as cell type. The lesions or defects may include microscopic perforations of the vascular wall, defects or perforations of endothelial cell walls, or defects of cell organelles, etc. The dose of radiation is emitted by a controllable radiation source and is therapeutically active, meaning it relates to the medical treatment of the condition. Without being bound by the following explanation, it appears that the majority of the cells affected by the radiation are only damaged to a degree that they are essentially still alive and not directly killed by the radiation. The region is damaged to an extent that the permeability for the chemotherapeutic and/or cytotoxic substance into the tissue to be treated is improved such that the substance can transpermeate and/or diffuse and/or extravasate from the supply portion (e.g. vessel) across the boundary wall to the tissue to be treated in a faster and/or easier, preferably essentially unhindered way.

The chemotherapeutic or cytotoxic substance could for instance be a noble metal complex such as a platinum-containing anti-cancer agent, e.g. selected from the group of carboplatin, oxaliplatin or cisplatin. The substance could also be a noble metal salt and/or a noble metal in the form of single nanoparticles, e.g. gold or silver nanoparticles, preferably in a coloidal suspension. Other alternatives are further second generation compounds such as oxaliplatin, picoplatin, satraplatin, etc.

The invention is preferably carried out by administering a preparation containing moderately cytotoxic substances. Advantageously, the preparation contains an alkylating antineopleastic agent, such as for example a derivative of the alkylating agent dacarbazine, preferably an imidazotetrazine derivative of the alkylating agent dacarbazine or procarbazine (Natulan®). The preparation according to an especially preferred embodiment contains temozolomide. Furthermore, a preparation containing one or more N-nitroso compounds, especially selected from the group of nimustine (ACNU), carbomustine (BCNU), lomustine (CCNU), and fotemustine (Muphoran®) is highly preferred as well.

It is especially advantageous, if the dose of radiation comprises several beams of microscopic cross-section, which are adapted to generate microscopically damaged regions in the at least one boundary wall structure of the supply portion of the tissue. The radiation preferably comprises several beams, whose cross-sections form at least one fan or array in at least one imaginary plane inside the tissue or on the tissue surface with each of the cross-sections being separate from each other on said plane.

A microbeam cross-section may exhibit an arbitrary shape, e.g. elliptical or square-like shape. Preferably it is of circular or of rectangular, i.e. slit-like shape. In the case of beams with a slit-like cross-section the damaged region exhibits a sliced or chopped pattern, whereas in the case of beams with a substantially circular cross-section, the damaged region appears rather punctured.

The characteristic width of the cross-section of a single microbeam, for the purpose of the current application called "aperture width" of a single microbeam, preferably lies in the range of 10 to 100 micrometers, more preferably 20 to 50 micrometers, most preferably about 25 micrometers.

According to a preferred embodiment of the present invention, a highly selective irradiation procedure is obtained when the microbeam parallel axes are spaced by a distance (inter-beam distance) from 100 to 400 micrometers, preferably 150 to 250 micrometers, and more preferably 190 to 210 micrometers.

Especially good results can be obtained when the radiation is provided by a synchrotron radiation source. In such a case, the one or more microbeams are preferably derived from pulsed synchrotron radiation by refracting, filtering and collimating as known to the person skilled in the art. Similarly good results can be obtained when the radiation is provided by an X-ray laser radiation source. Most preferably, a free-electron laser (FEL) is used in such a case, which similarly to a synchrotron provides a spectrum of Bremsstrahlung emitted by relativistic speed electrons which move freely through a magnetic structure. Also in such a case, the one or more microbeams are preferably derived from the FEL radiation by refracting, filtering and collimating as known to the person skilled in the art.

The method according to the invention provides higher selectivity of the radiation treatment by focusing at least one beam with microscopic cross-section, i.e. microbeam, on the vascular system of the tumor, i.e. the supply portion of the tumor tissue. By spatial parallel shifting of the axis of the at least one beam or by applying an array or a multitude of microbeams with spatially fixed axes, a multitude of microscopic lesions within the endothelial cell walls are caused. These damage regions increase the transpermeability of the wall as long as the damaged regions remain unhealed.

The localized effect of the substance is optimized by administering the preparation containing said substance to the patient after the transmittal of the dose of radiation, preferably by local intravenous administration. However, oral administration or other administration routes are also possible.

In order to achieve an especially advantageous synergistic conjunction of radiation treatment and drug delivery, the preparation is administered to the patient immediately after the irradiation by the array of microbeams has occurred, and prior to the moment, when the microscopic damage regions of the wall structure of the supply portion of the tumor tissue are completely cured. More preferably administration takes place between 40 and 300 minutes, and even more preferably between 45 and 150 minutes after radiation caused formation of the at least one microscopic damage region.

Administration methods and times can be varied according to the disease to be treated and the substances involved, and depend on the kinetics of the substances comprised in the preparation (time until the substance reaches its target). The crucial element is that the cytotoxic and/or chemotherapeutic substance reaches the site of damage before the damage is substantially or completely cured. In other words, the drug administered after transmittal of the dose of radiation must arrive at the defect during the time window during which the at least one microscopic damage region is still present (e.g. as long as the pores caused by microbeams are still open) and therefore can be permeated by the substance. Repair typically begins about 30 min to 4 hours after irradiation.

By quasi simultaneous "perforation", i.e. the time necessary to cause the at least one or the multitude of damage regions is at least one order of magnitude shorter than the time span of their healing, a chemotherapeutic time window is formed in which a preparation carrying at least one cytotoxic and/or chemotherapeutic substance reaches the site of damage in the form of microscopic damage regions and a cytotoxic dose of the at least one chemotherapeutic or cytotoxic substance transpermeates from the supply portion to the supplied portion of the diseased tissue predominantly by diffusing through the at least one microscopic defect formed in a boundary wall structure of the supply portion of said tissue. In order to obtain a high selectivity and a high ratio of the time of defect healing and the necessary time to cause the damage regions, the total beam exposure by a sum of microbeams is preferably less than 30 seconds, more preferably less than 3 seconds and most preferably less than 1 second.

Furthermore, a single microbeam pulse in the delivery the dose of radiation advantageously has a width of less than 1 second.

An especially advantageous effect can be achieved by transmitting to the patient a pulsed radiation collimated into arrays of highly parallel beams of microscopic cross-section, preferably with a low divergence. The focussing of the target tissue during radiation can be optimized by so-called "intensity modulated arc", "volumetric modulated arc", "rapid arc" or by "cross-firing", in which the tissue is irradiated by rays delivering an anisotropic radiation intensity field for instance by irradiation from different directions.

In this respect, also conventional therapeutic apparatuses, especially if combined with X-ray computer tomographic (CT) scanners or assisted by magnetic resonance image (MRI) scanners can be used to implement the present invention. However, the total energy transmitted by the sum of microbeams according to a further preferred embodiment of the invention preferably corresponds to the interval of 100 to 4000 Grays, preferably 150 to 2000 Grays, more preferably 190 to 310 Grays.

The high selectivity of the irradiation procedure is preferably increased by making use of a spectral range of the beam radiation from 33 to 600 keV and more preferably 50 to 350 keV.

Furthermore, the invention is preferably carried out with beam aperture widths of 10 to 100 micrometers, more preferably 20 to 50 micrometers and most preferably 25 micrometers.

The current invention suggests a symbiotic or synergistic combination of radiotherapy and chemotherapeutic drug delivery. Contrary to conventional radiotherapy, the radiation used essentially does not act in a cytotoxic way, in other words, it essentially does not have an antiproliferative effect on the diseased tissue or tumor tissue. The radiation used according to the current invention produces transiently damaged regions in the vascular walls so that the boundary i.e surrounding tumor tissue becomes more accessible to the applied agent (compound) instead of being directly "killed". Thereby, the radiation itself essentially does not have a lethal effect on the diseased tissue or tumor tissue, however, the permeability of the boundary vascular wall is increased, allowing the chemotherapeutic or cytotoxic substance to "diffuse" through the damaged regions across the wall to the supplied tissue and unfold its cytotoxic effect there. The effect of the current invention is surprising in that, contrary to the formerly used radiation with doses of several hundred, even thousand Grays (doubled in cross-fire mode), good results can be achieved by using radiation doses of generally about 10-50 times lower than microbeam radiation therapy (MRT) used for disease treatment so far. By combining this specific form of MRT, using concentrated discrete radiation at lower doses than in standard MRT-therapies, with the administration of chemotherapeutic substances, surprisingly good results in the terms of tumor regression were achieved. In particular, surprisingly good results were obtained when pre-treating the tumor tissue with short-term conventional radiotherapy prior to administering the dose of radiation according to the present invention.

The spectral range and the intensity of the microbeams may be chosen with respect to the specific tumor tissue to be irradiated, and therefore other types or sources of radiation may be used, e.g. ultraviolet, visual and infra-red highly collimated and parallel light sources, e.g. lasers, or beams of particles such as alpha, beta, deuteron, proton and heavy ion. The at least one (micro-)beam may therefore be a particle beam, or a light beam with a spectral range of ultra-violet and/or visible and/or infra-red light or combinations thereof. In case of light with a spectral range of X-rays, the radiation source of the at least one beam may be an X-ray emitter; preferably a magnetron, an X-ray tube or an X-ray-laser. The dose of radiation may also comprise combinations of different beam types.

Also the pulsing regime, the beam aperture width, meaning generally the characteristic size and the shape of the microbeam cross-section as well as the pattern of beam array, i.e. the number of microbeams in the array and their spacing, and the distances between the beam axes, shall be devised as to obtain a disease tissue specific- or tumor tissue specific and selective irradiation procedure as to fulfil the occurrence of the therapeutic time window in accordance with the present invention.

The preparation of the present invention and its delivery method can be used in a wide variety of treatments. The use of the delivery system is not only limited to cancer therapy, but can also be used in the treatment of other diseases. By this method, also antibodies, vectors, nanoparticles, such as gold- or other metal particles or release pellets and bits can be delivered to a specific site in the body which has been prepared for drug extravasation through regions damaged by specifically localized irradiation.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 1b depicts the occurrence of a sliced or chopped pattern of microscopic damaged regions caused by the microbeam irradiation in the wall structure of the supply portion of the tumor tissue according to the first embodiment shown in FIG. 1a;

FIG. 2b depicts the occurrence of a punctured pattern of microscopic damaged regions caused by the microbeam irradiation in the wall structure of the supply portion of the tumor tissue according to the second embodiment shown in FIG. 2a;

FIGS. 5-7 illustrate the vascular permeability in a U-87 MG mouse model of glioblastoma, wherein FIG. 5 illustrates a comparison of the degree of extravasation of CD-31 or FITC-dextran, respectively, between a MR-treated sample and a control group; and FIG. 6 shows a schematic comparison of the permeability index (ratio) in micro beam radiation treated (MRT) samples versus a control group;

FIG. 7 shows a tumor vessel ultrastructure of treated tumors versus a control group (transmission electron microscopy, CM 12);

DESCRIPTION OF PREFERRED EMBODIMENTS

The source of the primary beam used for the irradiation procedure should be able to provide the high required dose rates. Thus, synchrotron radiation sources are preferred, such as the National Synchrotron Light Source (NSLS) in the United States, the European Synchrotron Radiation Facility (ESRF) in Grenoble, France, and others from the list published under http://www.lightsources.org/regions. Alternative sources are radiation emitted from a free-electron laser, especially an X-ray laser, such as the XFEL of the DESY, the German Electron Synchrotron in Hamburg, Germany, or the SwissFEL of the Paul Scherrer Institute in Villigen, Switzerland, or others from the list published under http://sbfel3.ucsb.edu/www/v1_fel.html. But as more compact devices similar to those of conventional radiotherapy apparatuses may be advantageous, also Bremsstrahlung, radiation derived from particle deceleration or direct particle beam sources, such as e.g. in the microbeam radiation (MR) system proposed in the US-patent application US2010329413 A1, are suitable for the realization of the invention.

Figure 1A:
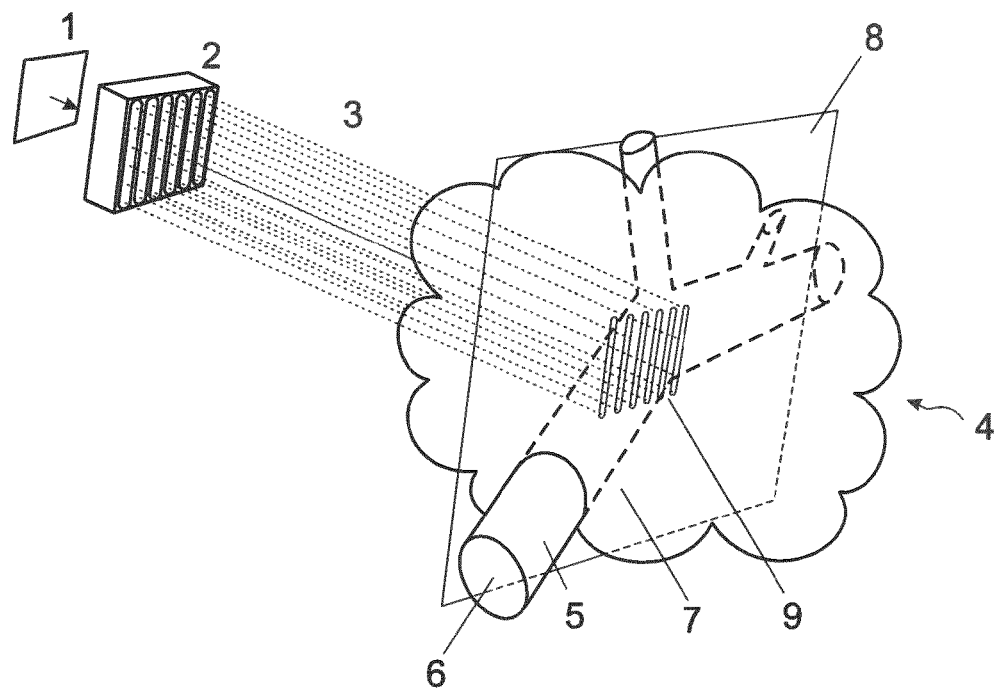
FIG. 1a shows a possible schematic setup for the microbeam array irradiation procedure according to a first embodiment of the present invention in which the microbeams have slit-like cross-sections.

In FIG. 1a, a typical setup for the microbeam radiation (MR) procedure according to a preferred embodiment of the present invention is shown. The primary beam 1 is deflected into direction of the biological tissue, e.g., the tumor tissue 4 to be treated. By means of a collimating device 2, a bundle of microbeams 3 with parallel beam axes is generated, where the beams exhibit slit-like cross-sections. In this way, the microbeam cross-sections form a fan-like array 9 in at least one imaginary plane 8 which is configured as a sectional plane through the tissue or on the tissue surface. The cross-sections are separate to one another. As depicted in FIG. 1a, it is preferable that the cross-sections are equally spaced in the fan-like array 9. According to the setup shown in FIG. 1a, the array 9 is focused on the wall structure of the supply portion of the tissue 5. The wall structure 5 separates the supply portion 6 of the tumor tissue 4 from the supplied portion 7 of the tumor tissue 4.

Figure 1B:
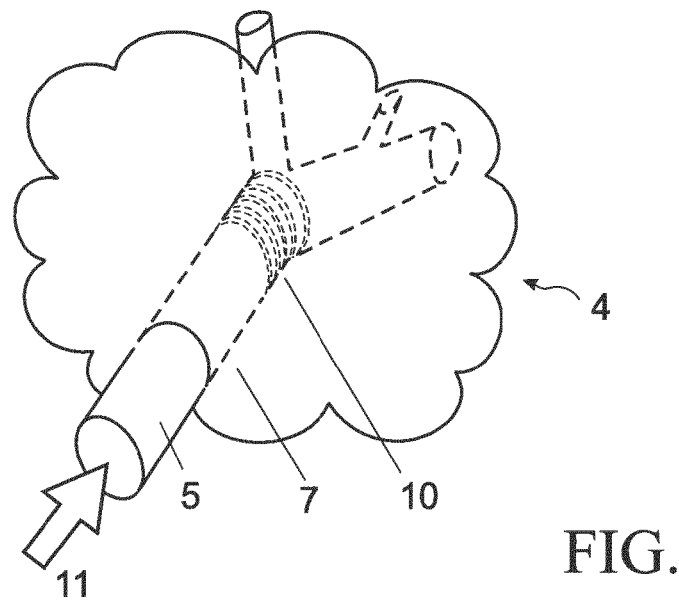
Figure 2A:
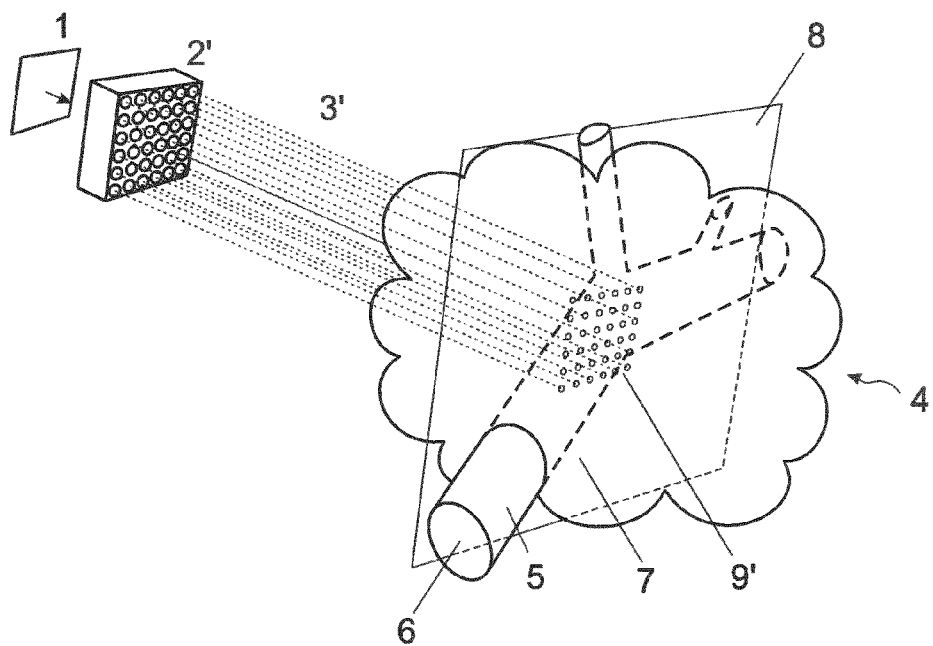
FIG. 2a shows a possible schematic setup for the microbeam array irradiation procedure in accordance with a second embodiment of the present invention in which the microbeams have rather circular microscopic cross-sections.

By means of the interaction of the array 9 of the microbeam bundle 3 with the wall structure 5, microscopic damage regions are formed in the wall as to cause an increased permeability of the wall from the supply portion 6 to the supplied portion 7 of the tissue 4. In FIG. 2a, another typical setup for the microbeam radiation (MR) procedure according to a second preferred embodiment of the present invention is shown. Again, the primary beam 1 is deflected into the direction of the tumor tissue 4 to be treated. Here, by means of a collimating device 2', a bundle of micro beams 3' exhibiting parallel beam axes is generated. In this way, the microbeam cross-sections form an array 9' in the at least one imaginary plane 8. Here, the beam cross-sections are separate to one another in the two dimensions of the plane 8. Again, it is preferable that the cross-sections are equally spaced in the array 9' and that the array 9' is focused on the wall structure of the supply portion of the tissue 5. Again, microscopic damage regions are formed in the wall causing an increased permeability of the wall from the supply portion 6 to the supplied portion 7 of the tissue 4. Contrary to the first embodiment according to FIGS. 1a and 1b, the second preferred embodiment according to FIGS. 2a, 2b of the present invention leads to an irradiation procedure rather puncturing than chopping the wall structure 5 of the collimated microbeams 3'.

Figure 2B:
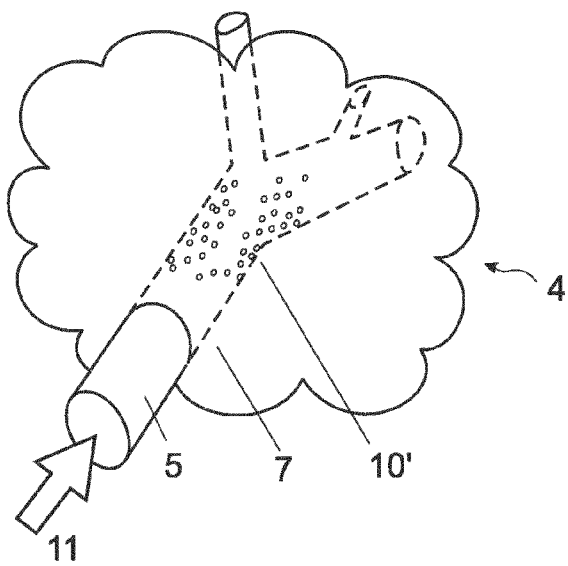

The choice of chopping (by the fan-like array 9 of microbeams according to the first preferred embodiment) or rather puncturing microbeam irradiation (by the array 9' according to the second embodiment) may be used to control or vary the depth and/or width of permeation into the tissue 4. The occurrence of damage regions 10 and 10' is illustrated in FIGS. 1b and 2b, respectively. Thus subsequent to the MR procedure and prior to the moment, when the microscopic damage regions 10, 10' in the wall structure 5 of the supply portion of the tumor tissue are completely cured, a preparation carrying cytotoxic substances 11 is administered to the supply portion 6. The preparation preferably is made up conventionally, typically in pyrogen-free, sterile saline, and typically for intravenous injection, as is known to the person skilled in the art.

As the preparation is administered, a lethal dose of the cytotoxic substances 11 transpermeates from the supply portion 6 through the microscopic damage regions 10, 10' to the supplied portion 7 of the tissue 4 which is to be intoxicated.

Example 1

Chick chorioallantoic membranes (CAM) were irradiated at the biomedical beamline of the European Synchrotron Radiation Facility (ESRF). Here, the "ID17" wiggler source has its critical energy at 33 keV, with the entire spectrum extending to over 350 keV. A white beam filtered spectrum is required to achieve very-high-dose rates of up to 80 Grays/sec/mA. The filtering of 1.5-mm carbon, 1.5-mm aluminium and 1-mm copper allows cutting the low-energy spectrum of the synchrotron radiation below roughly 50 keV. The wiggler source provides, at a distance of 34 m from the storage ring, a primary beam of up to approximately 20 mm in width and 0.5 mm in height. The production of microbeams with aperture widths of 25 micrometers, with a 200 micrometer center-to-center spacing for full width half maximum-sized beams, was realized by the use of the Archer variable multi-slit collimator, delivering, after the passage through 16 mm of aluminium, peak entrance dose values in the range of several hundreds of Grays at a typical dose rate of approx. 40 Grays/sec/mA. The approximately 10 mm×10 mm wide fan-like bundle or array of 50 microbeams was applied to irradiate CAM in a petri dish, scanning vertically over 1 cm, starting 1 mm above the bottom of the petri dish, covering more than the height of the entire CAM. As such, the surface doses at the entrance to the petri dish were 100 Gray, which accounts for a dosis of approximately 2 Gray per microbeam. A GafChromic radiochromic film type HD-8ID (lSP Corporation, Wayne, N.J. 07470 USA) was laid over the surface of CAM prior to irradiation for one second.

Figure 3:
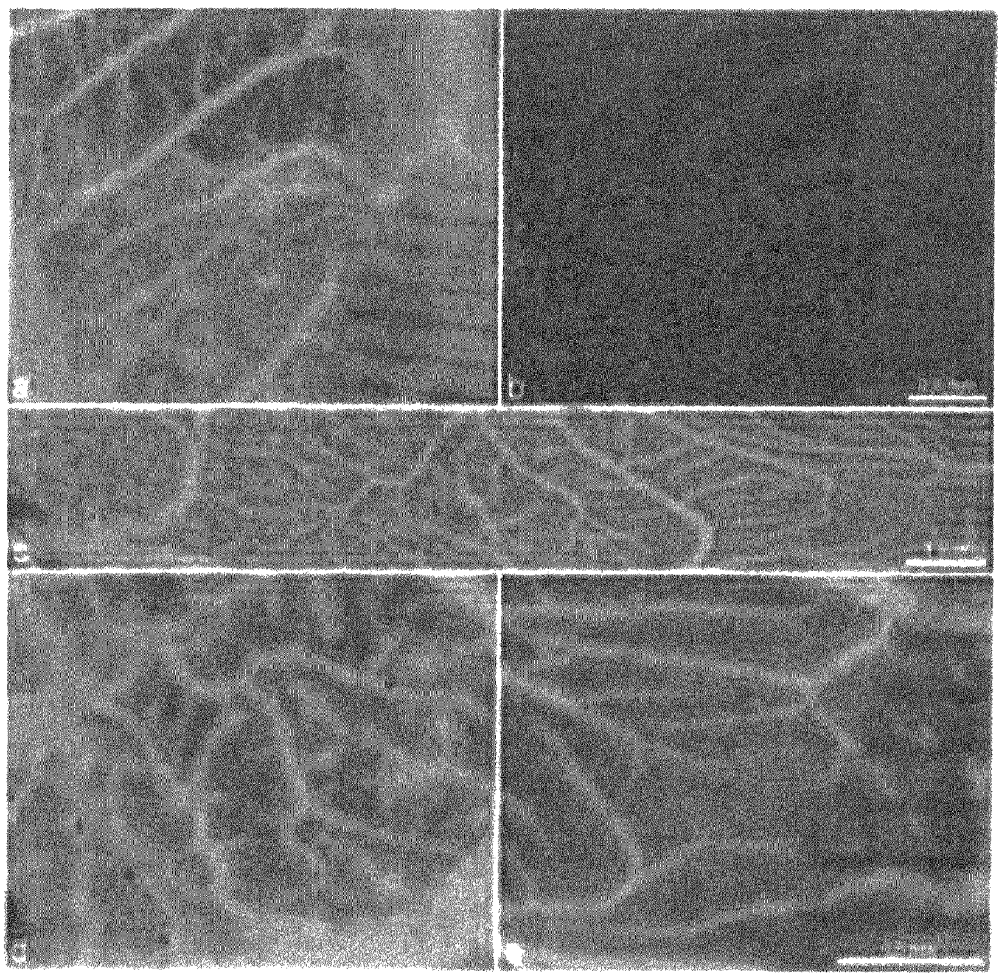
FIG. 3 illustrates the increased permeability of normal chick chorioallantoic membrane (CAM) being irradiated as a model tissue to simulate the vascular wall structure in the supply portion of a tumor (FITC-dextran MW 2,000,000 as green-fluorescent marker, using a LEITZ DM RBEmicroscope)
Figure 4:
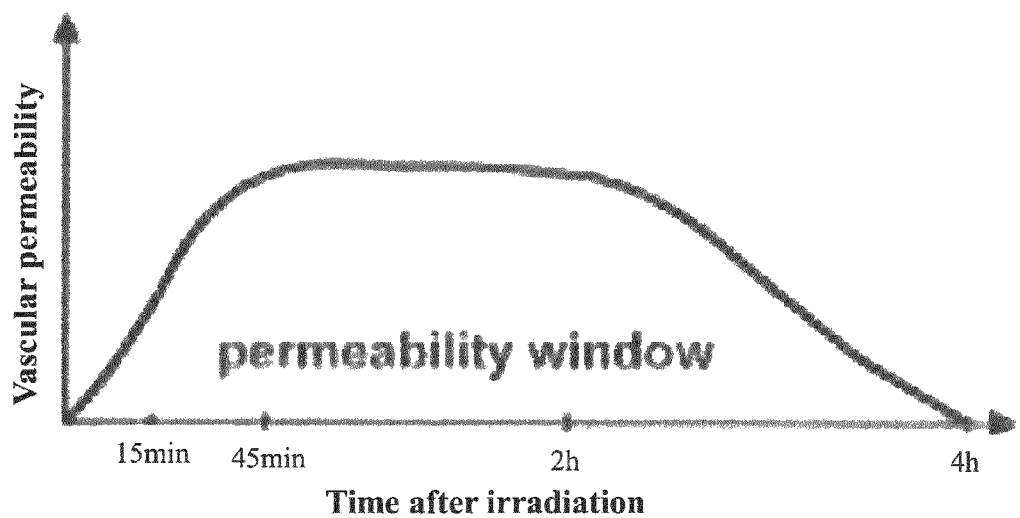
FIG. 4 shows a schematic representation of the vascular permeability over time after irradiation.

The caused increased vascular permeability of the membrane, being a biological model for the wall structure of the supply portion of the tissue to be treated is illustrated by FIG. 3. FIG. 3 shows the permeability forty-five minutes after MR treatment and after treatment with vascular endothelial growth factor (VEGF), stimulating cells to build new vessels i.e. angiogenesis. FIG. 4 shows that the vascular permeability increases in the period between 15 minutes and 240 minutes after the MR procedure, while permeability is dramatically increased between 40 and 150 minutes after MR procedure has initiated the formation of vascular damage regions. This is demonstrated in FIGS. 3a and 3b. In FIG. 3a, the extravasation of fluorescein-isothiocyanate-(FITC)-dextran results in green-fluorescent halos in the area irradiated by the microbeam array as indicated by the radiochromic film. Rhodamine beads of a characteristic diameter of 100 nanometers, however, do not diffuse into the surrounding tissue and remain affixed as red fluorescent dots along the microbeam propagation lines, as shown in FIG. 3b.

FIGS. 3d and 3e are micrographs at higher magnification respectively left and right parts of the region depicted in FIG. 3c. FIGS. 3c and 3d show that at the site of application of Thermanox coverslip treated with VEGF (indicated by asterisks in the left hand side of FIGS. 3c-d), the vascular permeability increases faster, i.e. already at 20 to 25 minutes after the MR treatment, as demonstrated by FITC-dextran extravasations (some indicated by arrows in FIGS. 3c and 3d. While in the zone without VEGF treatment (shown in the right part of FIG. 3c and its higher magnified version in FIG. 3e, no further increase in vascular permeability has been detected.

Figure 5:
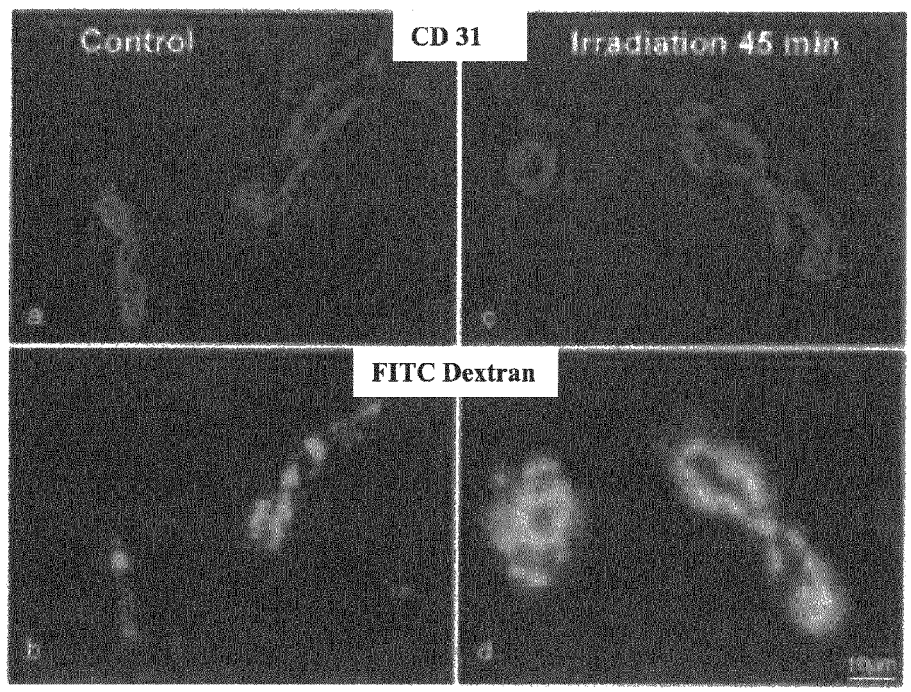

Furthermore, no extravasation of the green fluorescent FITC-dextran 2'000'000 compound was observed in the control tumors (see FIGS. 5a and 5b), as no radiation-defects were present which would have allowed extravasation, while in the MR treated zone (see FIGS. 5c and 5d), a clear halo of green fluorescence is visible due to such extravasation through the microscopic damage regions. Here, the MR treated tumor tissue (FIG. 5c) and the blood vessels in control (FIG. 5a) stained with platelet endothelial cell adhesion molecule-1 (CD-31) are red-fluorescent and the intravascular FITC-dextran in 5b and extravasated FITC-dextran in 5d is green (FIGS. 5d and 5b), respectively.

Figure 6:
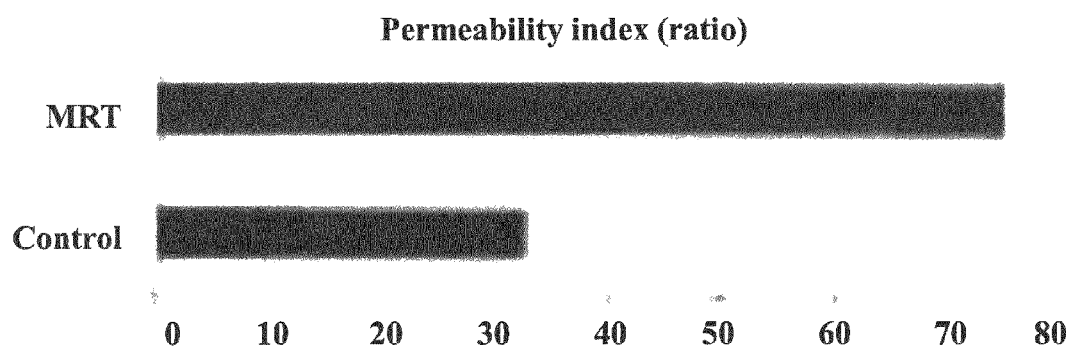

In addition, FIG. 6 provides the quantification of the vascular permeability in controls and MR-treated tumors as a ratio of extravasated FITC-dextran fluorescent area per vessel area.

Figure 7:
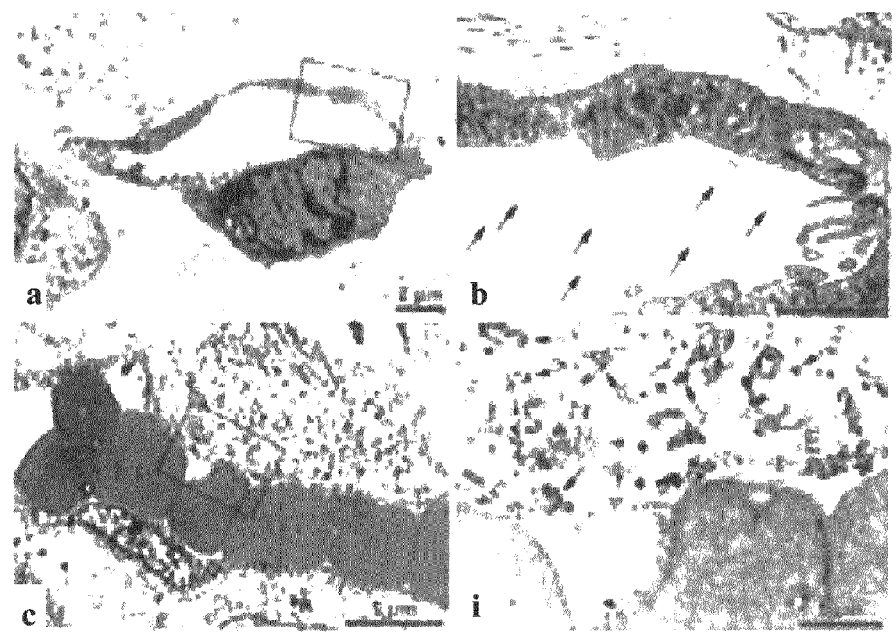

FIG. 7 shows a tumor vessel ultrastructure (Transmission electron microscope CM 12). This reveals a normal morphology in the control tissues as shown in FIG. 7a and its higher magnification of the selected area in FIG. 7b) with no extravasation of FITC-dextran (intraluminal dark dots, indicated by arrows). Conversely, in treated tumors shown in FIG. 7c and in its higher magnification of the selected area in FIG. 7d), an extravasation of the fluorescent probe was observed as dark dots (arrows) in the extravascular space. Here, the signs "E" represent disrupted endothelia containing multiple vacuoles of different sizes (indicated by asterisks) and the symbols "Er" indicate the presence of erythrocytes.

Figure 8A:
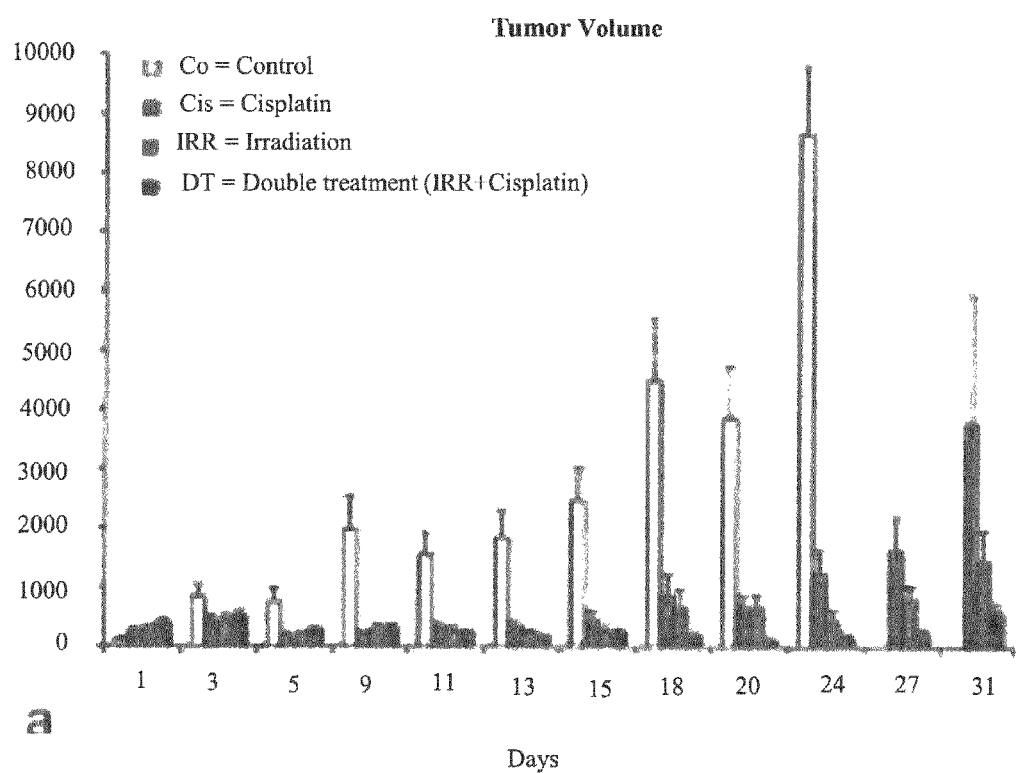
FIG. 8a represents a schematic comparison of tumor volumes between differently treated animals (U-87 MG human glioblastoma xenographs in Balb/c nude mice) after a single chemotherapeutic treatment with cisplatin; after treatment by irradiation only, by irradiation followed by cisplatin according to a preferred embodiment of the present invention, and a control group.
Figure 8B:
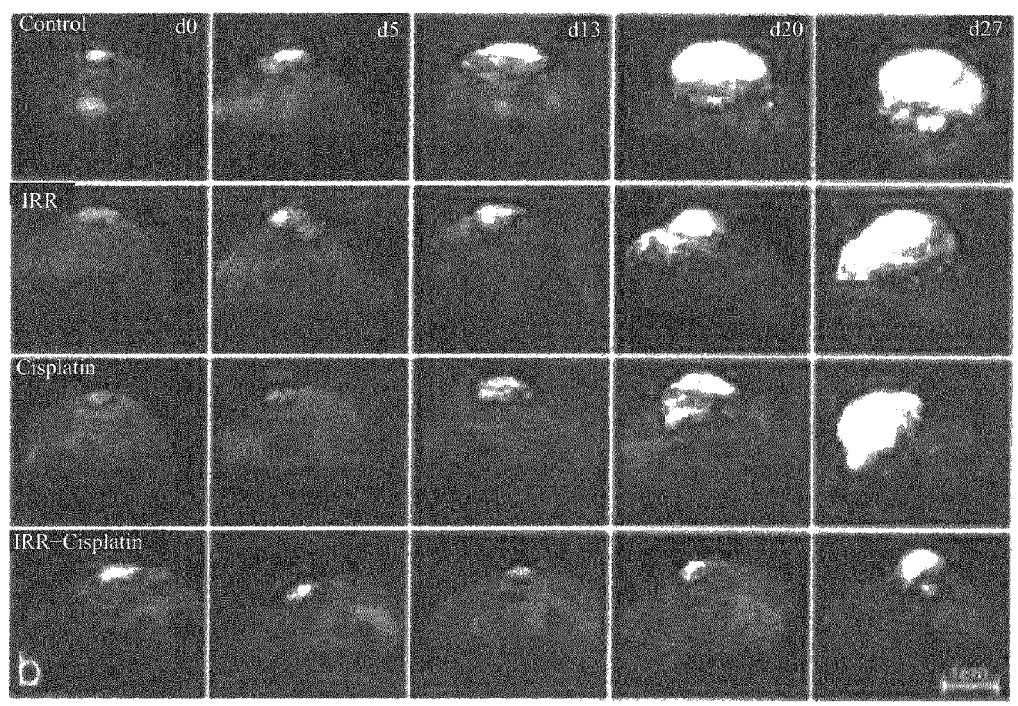
FIG. 8b shows magnetic spin resonance images of tumors (U-87 MG human glioblastoma xenographs in Balb/c nude mice) after a single chemotherapeutic treatment with cisplatin; after treatment by irradiation only, by irradiation followed by administration of cisplatin according to a preferred embodiment of the present invention, and images of a control group.

The efficiency of the present method is most evident when comparing tumor volumes as shown in FIG. 8a and magnetic spin-resonance images of the tumors as shown in FIG. 8b. In the double treatment (DT)-group (far right column of each group) having been treated by administering Cisplatin (Cis) after the MR procedure, when using the chemotherapeutic window of increased vascular permeability (compare with FIG. 4), the tumor sizes showed a progressive and significant decrease after treatment. Besides the uncontrolled growth of control tumors (Co) (far left column of each group up until day 24, no filling), the single therapeutic steps of either only Cisplatin (Cis) (second column from left in each group until day 24, far left column for day 27 and 31) or only irradiation (IRR) according to MR treatment (second column from right in each group until day 24, middle column for day 27 and 31), showed a gradual increase in size. Accordingly, anatomical MR imaging from zero to 27 days after treatment showed a significant decrease in size in the tumors having received the symbiotic treatment according to the present method of the invention when comparing with the other experimental groups.

Example 2

In this example, CAM were irradiated at the biomedical beamline of ESRF. The generation and preparation of the microbeams occurred basically in the same manner as described in Example 1 according to a second preferred embodiment with the substantially circular cross-section of each microbeam. The difference here however is that behind the multi-slit collimator a second collimator (such as an Archer variable multi-slit collimator) was placed into the path of the first array of microbeams formed by the first collimator. The slits of the additional collimator were rotated by 90 degrees so as to chop the microbeams exiting the first collimator into an array of 50×50 beams with aperture widths and heights of both 25 micrometers and a 200 micrometer center-to-center spacing for full width half maximum-sized beams.

The approximately 10 mm×10 mm wide array of 50×50 microbeams was applied to irradiate CAM in a petri dish. A GafChromic radiochromic film type HD-81D (ISP Corporation, Wayne, N.J., 07470 USA) was laid over the surface of CAM prior to irradiation for one second. Due to the chopping of the first fan-like array of micro-beams into the array of 50×50 beams, the approximate surface doses at the entrance to the petri dish were 12 to 25 Gray, which accounts for a single microbeam dosis of approximately 0.25 to 0.52 Gray.

As a result, the extent of increase in vascular permeability is similar to that shown in FIG. 3 for Example 1. But in Example 2 the irradiation rather punctures the tissue. Therefore, the level of exposure of the irradiated tissue is even less lethal and results in a much narrower chemotherapeutic window (compared to FIG. 4). Even when Cisplatin (Cis) is administered within 30 min to 1 h after irradiation, the glioblastoma tumor sizes show a progressive and significant decrease after treatment.

Furthermore, this example shows that the second preferred embodiment of irradiation by the array of beams is especially advantageous for the treatment of lung tissue tumors, as lung tumors are most commonly carcinomas that derive from epithelial cells, which are less dependent on the endothelian growth, as in the case of glioblastomas. Therefore, the less lethal but puncturing perforation in the treatment of lung tumors, especially by cross-firing, results in a preferable method of treatment.

Example 3

According to a third preferred embodiment, CAM were irradiated at the biomedical beamline of ESRF only after the tissue was irradiated by a conventional radiotherapeutic apparatus (e.g. the Rapid Arc by VARIAN using a dynamic multileaf collimator for providing a variable dose rate and variable gantry speed). The homogenous delivery of 6 MeV to 10 MeV irradiation for 2 to 10 min resulting in 4 Gray for filtered radiation to 20 Gray for filter-free radiation to the tissue, seems to induce a perfectly intact but "hibernating" tissue. In other words, the ability for vascular endothelial growth is drastically reduced. Irradiating the hibernating tissue then with the fan-like array of microbeams according to Example 1 or with the array of microbeam according to Example 2, in the case of CAM, the window of increased vascular permeability is extended.

Example 4

The experimental setup and procedure of Example 1 was also applied to study the effect of the present invention on malignant lung tissue in a mouse-model of lung carcinoma, in which case the tumor growth is mainly derived from epithelial cells. The applied combined treatment dramatically reduced the tumor growth and increased the animal survival rate, surprisingly without the occurrence of lung fibrosis which is a unique result when compared to other types of treatment.

The use of the substance in the inventive method and its examples of a preferred realization as described above, result in a more effective treatment of tumor tissue. The administration method can be used, for example, in the cancer treatment of humans having e.g. brain or lung tumors, and possibly even in intra-operative radiation therapy. It is also envisioned that the substance and its administration method according to the invention can be used for cancer research in animal models. The delivery strategy of drug substances, which has a broad spectrum of applications could be applied for instance to the treatment of different pathological processes in different organs, e.g. tumors of the brain, especially of glioblastoma, of the lung, or the spinal marrow, by using different compounds, such as nanoparticles, preferably noble metal particles, e.g. gold nanoparticles, moderately toxic chemotherapeutics as well as antibodies and vectors, etc.

LIST OF REFERENCE SIGNS 1 primary beam
2, 2' collimating device
3, 3' bundle of microbeams
4 tumor tissue
5 wall structure
6 supply portion of 4
7 supplied portion of 4
8 imaginary plane
9, 9' array of 3 or 3', respectively
10, 10' (microscopic) damage regions, defects caused by irradiation
11 preparation carrying cytotoxic substance(s)

The invention claimed is:

1. A method of treating a cancer in a mammalian patient by a radiation therapy comprising the following steps in order:
transmitting a non-cytotoxic dose of radiation to a tumor tissue, wherein the dose of radiation comprises short pulsed radiation collimated into arrays of highly parallel beams of microscopic cross-section provided by a synchrotron radiation source, which are adapted to generate at least one microscopic damage region in at least one boundary wall structure of a supply portion of the tissue, the supply portion being a blood vessel, and wherein during the delivery of the dose of radiation a total beam exposure by the sum of microbeams is less than 30 seconds; and
subsequently administering a preparation comprising at least one chemotherapeutic or cytotoxic substance to the patient after the transmittal of the dose of radiation, such that the chemotherapeutic or cytotoxic substance reaches the at least one microscopic damage region before the at least one microscopic damage region is completely cured by endogenous tissue repair.

2. The method of treating according to claim 1, wherein the cancer is a brain tumor or a lung tumor.

3. The method of treating according to claim 1, wherein the chemotherapeutic or cytotoxic substance is a platinum-containing anti-cancer agent, selected from the group of carboplatin, oxaliplatin or cisplatin.

4. The method of treating according to claim 1, wherein the preparation contains an alkylating antineoplastic agent.

5. The method of treating according to claim 4, wherein the chemotherapeutic or cytotoxic substance contains temozolomide.

6. The method of treating according to claim 1, wherein the at least one microscopic damage region comprises at least one microscopic perforation.

7. The method of treating according to claim 1, wherein the dose of radiation is conveyed by at least one particle beam or at least one light beam having a wavelength in the spectral range of X-ray, ultra-violet, visible or infra-red light, or combinations thereof.

8. The method of treating according to claim 1, wherein the preparation is administered to a patient by local intra-venous administration.

9. The method of treating according to claim 1, wherein the preparation is administered to the patient between 40 and 300 minutes after radiation.

10. The method of treating according to claim 1, wherein a single microbeam pulse in the delivery of the dose of radiation has a length of less than 1 second.

11. The method of treating according to claim 1, wherein the total energy transmitted by the sum of microbeams in the delivery of the dose of radiation corresponds to the interval of 100 to 4000 Grays.

12. The method of treating according to claim 1, wherein in the delivery of the dose of radiation the microbeams have parallel axes which are spaced by an inter-beam distance from 100 to 400 micrometers.

13. The method of treating according to claim 1, wherein in the delivery of the dose of radiation a spectral range from 33 to 600 keV is used.

14. The method of treating according to claim 1, wherein in the delivery of the dose of radiation an aperture width of a single microbeam lies in the range of 10 to 100 micrometers.

\* \* \* \* \*